United States Patent [19]

Friesdorf et al.

[11] Patent Number: 5,140,519
[45] Date of Patent: Aug. 18, 1992

[54] METHOD FOR MONITORING PATIENT DATA AND CIRCUIT ARRANGEMENT THEREFOR

[75] Inventors: Wolfgang Friesdorf, Langenau; Martin Ryschka; Jörg Bayerlein, both of Stockelsdorf, all of Fed. Rep. of Germany

[73] Assignee: Drägerwerk Aktiengesellschaft, Lübeck, Fed. Rep. of Germany

[21] Appl. No.: 352,392

[22] Filed: May 16, 1989

[30] Foreign Application Priority Data

May 19, 1988 [DE] Fed. Rep. of Germany ....... 3817052

[51] Int. Cl.$^5$ ............................................. G06F 15/42
[52] U.S. Cl. ............................ 364/413.03; 364/224.6; 364/922.3
[58] Field of Search ...................... 364/413.02, 413.03, 364/413.04, 200, 900, 413.05, 413.06

[56] References Cited

U.S. PATENT DOCUMENTS

| | | | |
|---|---|---|---|
| 3,374,461 | 3/1968 | Anderholm et al. | 364/900 |
| 3,725,866 | 4/1973 | Oldfield, Jr. et al. | 364/200 |
| 3,737,863 | 6/1973 | Rowland et al. | 364/200 |
| 3,765,009 | 10/1973 | Graves et al. | 340/747 |
| 3,811,040 | 5/1974 | Weinfurt et al. | 340/721 |
| 3,835,455 | 9/1974 | Abbenante | 364/900 |
| 3,925,762 | 12/1975 | Heitlinger et al. | 340/870.09 |
| 3,960,140 | 6/1976 | Buxton | 340/870.24 |
| 3,970,996 | 7/1976 | Yasaka et al. | 364/900 |
| 4,051,522 | 9/1977 | Healy et al. | 340/721 |
| 4,232,682 | 11/1980 | Veth | 364/413.03 |
| 4,356,475 | 10/1982 | Neumann et al. | 364/413.02 |
| 4,409,652 | 10/1983 | Neumann et al. | 364/200 |
| 4,426,644 | 1/1984 | Neumann et al. | 340/722 |
| 4,695,955 | 9/1987 | Faisandier | 364/413.03 |
| 4,729,381 | 3/1988 | Harada et al. | 364/413.03 |
| 4,786,476 | 1/1988 | Graves et al. | 340/747 |
| 4,794,934 | 1/1989 | Motoyama et al. | 364/413.02 |
| 4,847,785 | 7/1989 | Stephens | 340/722 |
| 5,012,411 | 4/1991 | Policastro et al. | 364/413.06 |

OTHER PUBLICATIONS

Publication of the Deutsche Abbott GmbH entitled "Abbott-Narkosesimulator" by Helmut Schwilden of the Institute for Anesthesiology of University Bonn (Dec. 1986).

Thomas, Jr. et al., "Continuous Monitoring of Physiologic Variables with a Dedicated Minicomputer", *Computer*, pp. 30–35 (Jul. 1975).

Kalinsky et al., "Use of a Mobile Computer Cart for Cardiovascular Monitoring and Clinical Investigation", Conference: Computers in Cardiology, Rotterdam, Netherlands (Sep. 29–Oct. 1, 1977).

*Primary Examiner*—Gareth D. Shaw
*Assistant Examiner*—Matthew C. Fagan
*Attorney, Agent, or Firm*—Walter Ottesen

[57] ABSTRACT

A method of monitoring patient data generates an optimal overview. The patient data is sensed by appropriate sensors and displayed as parameter values assigned to individual organ systems. A data field contains a plurality of parameter values and overview graphic images referring to organ systems are formed from this data field with the aid of a network switch and are displayed in response to a retrieval command.

10 Claims, 3 Drawing Sheets

METHOD FOR MONITORING PATIENT DATA AND CIRCUIT ARRANGEMENT THEREFOR

FIELD OF THE INVENTION

The invention relates to a method for monitoring patient data which can be assigned to individual organs and organ systems as parameter values. The data is sensed by means of respective sensors. An advantageous circuit arrangement for carrying out the method is also provided.

BACKGROUND OF THE INVENTION

The monitoring of patient data such as data of the lung or of the cardiovascular system is known in many configurations by indicating monitoring apparatus.

An anesthesia simulator is disclosed in the publication "Abbott-Narkosesimulator" by Helmut Schwilden (Deutsche Abbott GmbH, Dec. 1986). In this anesthesia simulator, the possible vaporizer adjustment of the anesthesia apparatus is coupled to parameters of the ventilating system and certain physiological quantities of the patient with the said of a computer. The percentage of the cardiac output with which the individual organs are perfused is shown after adjustment of the data of the patient and of the anesthesia apparatus essential for the anesthesia as well as after the selection of the anesthesia substance. Each organ is assigned two quantities, namely, the percentage portion of the organ relative to the overall body volume and the percentage of the cardiac output with which this organ is perfused. This is concerned with the division of a measurement parameter determined as a patient value such as of the cardiac output (HMV) to the most important organs and with the image-like illustration of this division. In this way, the same measurement quality is generated from few patient data by means of the subdivision of a plurality of component data.

SUMMARY OF THE INVENTION

It is an object of the invention to provide a method for sorting a plurality of patient data and displaying or illustrating the same such that a previously determined display format is provided which is optimally adapted to the patient as well as to the treating physician. It is also an object of the invention to provide a circuit arrangement for carrying out the method. The advantage of such a predetermined display form is that a sorting of data pursuant to medical viewpoints is provided in lieu of an incomprehensible amount of data which is monitored and displayed such as with the intensive care of patients. This makes possible an optimal overview so that the actual condition of the patient can be judged both quicker and more reliably.

According to a feature of the invention, overview display images referring to an organ system are formed from a data field containing a plurality of parameter values with the said of a network switch and are read out by means of a retrieval command.

The indication of parameter values referring to an organ system can advantageously have a curved form and be presented as a function of its time-dependent course. From the time-dependent course of the parameter values, a display quantity can be determined which can advantageously represent the trend as may be required.

In a further embodiment of the invention, alarm announcements can be derived from the course of the parameter referring to the organ system. These alarm announcements can be advantageously arranged in accordance with levels of urgency and can be made realizable by means of different displays or display means.

The overview graphic images referring to an organ system can advantageously be so selected that they display the actual condition of the patient at the point in time of the retrieval command. In combination with the available storage elements, an inquiry can however be so set that an overview of a previous time duration is displayed at the time point of the inquiry. This time duration can be several hours or several days.

In a practical configuration, it is advantageous to generate at least overview graphic images with corresponding parameters of the following: consciousness/central nervous system (CNS), respiratory system, cardiovascular system and the metabolic system. The classification of the overview graphic images is in accordance with the clinical practice; however, it can be modified in correspondence to the wishes of the treating physician. It is also advantageous to store values characterizing the therapeutic plan and to display the same with respect to the corresponding organ system by command.

According to another feature of the invention, the parameter values are stored in several storage fields in the memory unit of the computer and selection in connection with the memory unit is possible for selecting organ systems and for selecting the treating variables.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
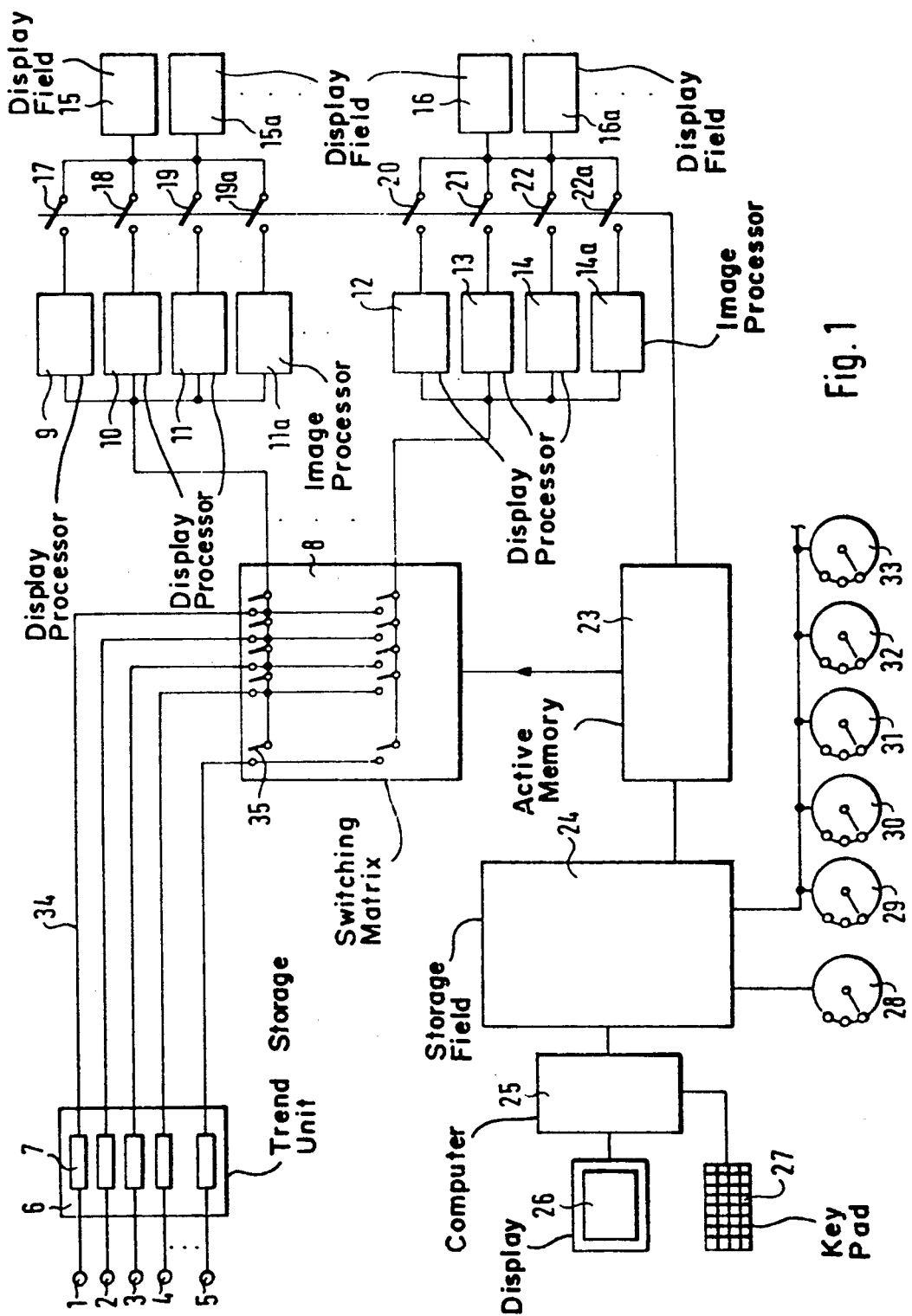
FIG. 1 is a circuit block diagram of an embodiment of the circuit arrangement according to the invention.

The schematic block diagram of FIG. 1 serves, for example, to indicate and/or illustrate the measured values scanned by five sensors 1 to 5 on display fields (15, 16) in individual organ system dependent overview display images in such a manner that a display format is provided which is previously determined and is optimally adapted to the patient's condition as well as to the physician.

The sensors 1 to 5 can, for example, monitor the following: blood pressure, heart rate, oxygen saturation, end expiratory carbon dioxide, temperature and the like. The signals from these sensors are conducted to a trend storage unit 6 which is provided with a trend memory 7 for each of the signals. The signals are sampled at a fixed clock frequency and stored. The trend memories 7 can be read out and their data reach a switching matrix 8 via connecting lines 34. At the switching matrix 8 and because of the switch position of a plurality of parameter selection switches 35, a selection can be made as to which data from the trend memories should reach the display processors 9 to 14. The display processors 9 to 14 prepare the content of the trend memories 7 for the desired display form and conduct the same to the display fields (15, 16). The display fields can be provided in any desired quantity.

Accordingly, the display processor 9 can, for example, generate a trend curve on the display field 15 from the trend content of the trend memory 7. The display processor 10 can provide a table in which the numerical values are imaged. The display processor 11 can generate a further desired display form referring to organ systems. By means of the corresponding switches 17 to 19, a selection can be made as to which display processor is to be switched to the corresponding display field, for example, display field 15. Each trend storage content of each sensor can be displayed in the desired display form on each display field (15, 16); (15a, 16a) with the aid of the switch combinations of the switching matrix 8 in combination with the coordinating switches (17 to 22); (19a, 22a).

Figure 3:
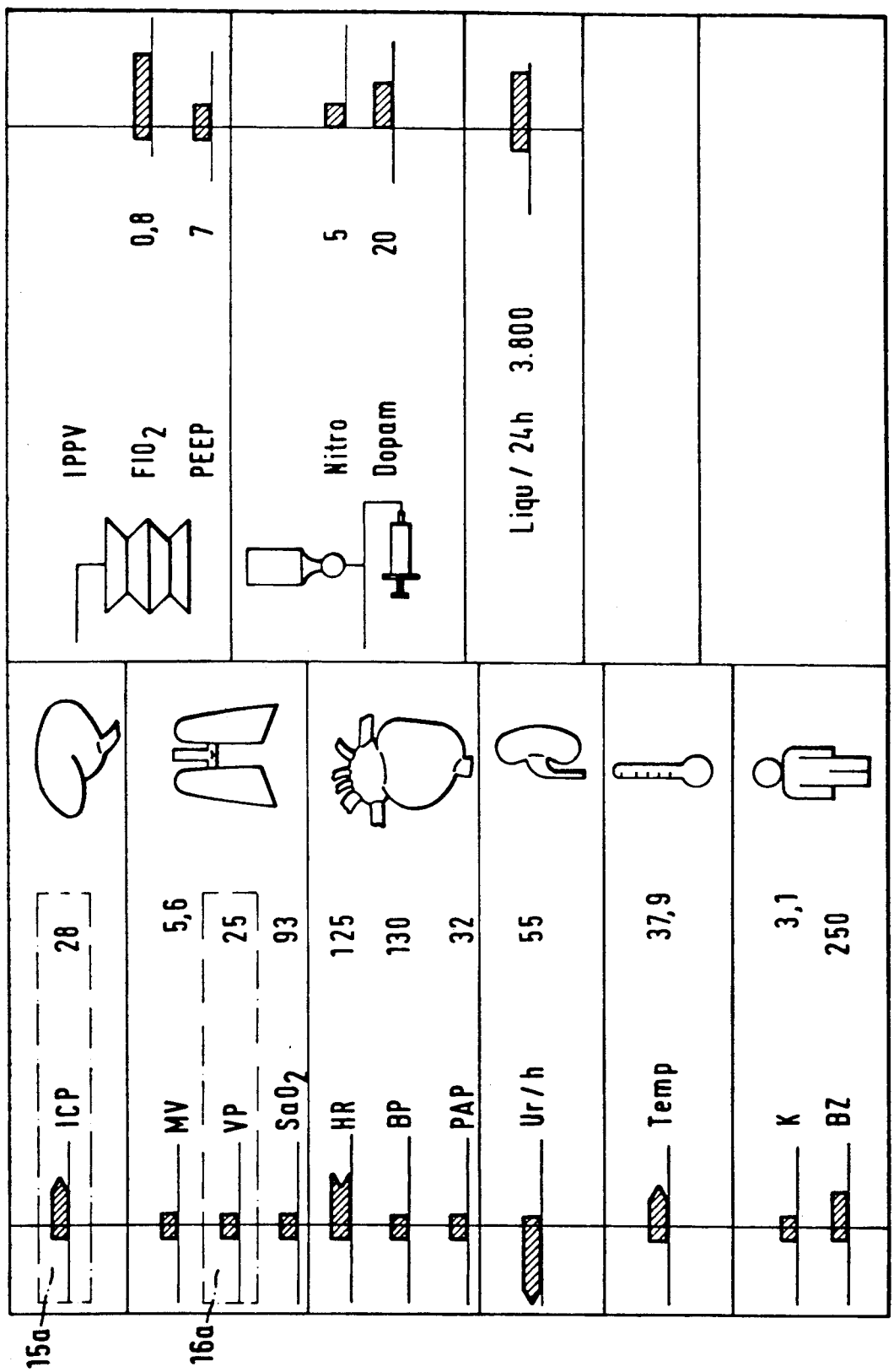

In addition, image processors (11a, 14a) can, by appropriate assignment of the switching matrix 8, be so supplied with patient data that the display fields (15a, 16a) contain respective extracts of the patient data referring to respective organ systems so that a complete overview of the patient condition is provided from a composite of these display fields (15a, 16a) as shown, for example, in FIG. 3.

Figure 2:
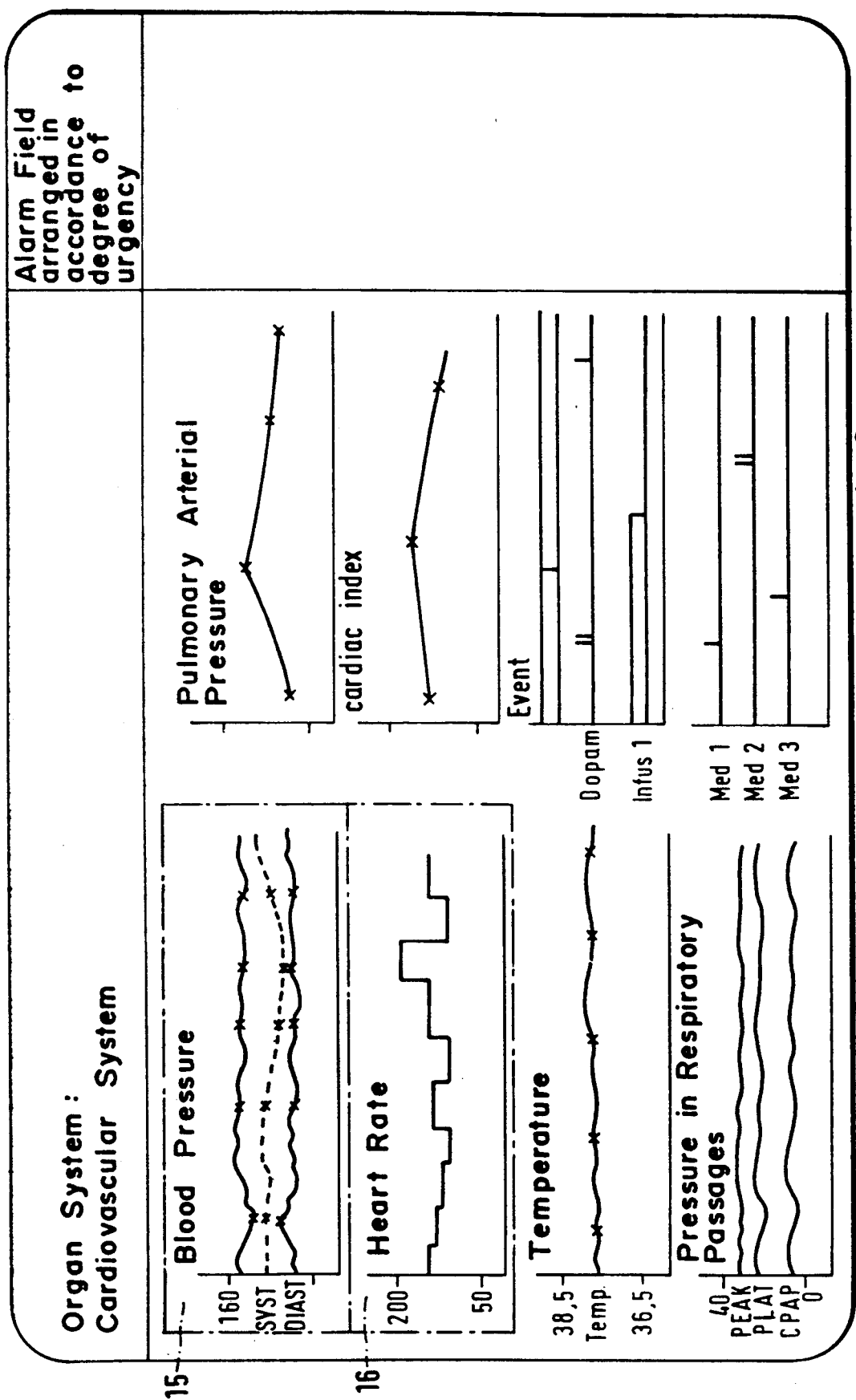
FIG. 2 is an overview graphic image of the cardiovascular system displayed with the circuit arrangement of FIG. 1; and, FIG. 3 is an overview image generated with the circuit arrangement of FIG. 1 in the form of an extract of different overview graphic images referred to respective organ systems.

In addition, a large number of fixed switching combinations of the switching matrix 8 are stored in a storage field 24. Each individual one of these switching combinations can be stored in the active memory 23 whose storage outputs influence the inputs of the switching matrix 8 as well as directly the coordinating switches (17 to 22). In dependence upon the content of this active memory 23, an overview graphic image is displayed in the display fields (15, 16) such that an organ system dependent selection is made from the sensor signals such as for the cardiovascular system (see FIG. 2). With the said of the image selection switches (28 to 33), a very specific combination can be selected and stored in the active memory 23 from the large number of switching combinations of the storage field 24.

The image selection switches (28 to 33) can be freely assigned as desired.

Different organ system images are selectable with the image selection switch 28. For example, the following can be adjusted: the overview graphic image of the cardiovascular system; the overview graphic image of the respiratory system; the graphic image of the balance of water and electrolytes; and the like. The predetermined parameter values, which were selected for the individual overview graphic images, are displayed simultaneously.

The selection of the information is apportioned amongst the image selection switches.

A typical diagnosis such as multitrauma, abdominal operation or cardiac infarction can be preselected with the image selection switch 29. The image selection switch 30 makes possible a selection according to individual days of hospitalization, for example, in position 1, the first hospital day; position 2, two to four hospital days; position 3, five to twenty hospital days can be displayed since the information important for the physician can also be dependent upon the number of days of hospitalization.

The image selection switch 31 makes possible the selection of a configuration specific for the clinic such as the combination of different kinds of treatment. This clinic configuration is essential for a specific area of application and can, however, be varied from clinic to clinic. With the image selection switch 32, different preferences in the combination of parameters can be selected in accordance with the selection of the operating person such as the head of a particular medical department. In this way, individual desires of the user can be accommodated.

With the image selection switch 33, the characteristics for the particular patient can be considered which, as may be required, can be a criteria for the information selected. Important variables include: sex, age, body weight and the like.

The variables of the image selection switches (29 to 33) can, as required, also be automatically selected if the image selection switch is connected with a computer system which administers data taken from the personal medical file since all parameters are included in the content of such a patient file.

The content of a large number of the stored combinations of the storage field 24 can advantageously be fixedly programmed such as the result of a scientific study; however, this can be changed at any time by the user as required. Such a change can be carried out with a computer 25 connected thereto which, in turn, is connected to a display unit 26 and to a key pad 27. In this way, each storage location of the storage field 24 can be called up and modified as required and again be stored.

This provides a substantial flexibility which on the one hand makes it possible without much complexity to obtain the desired selection of information simply by actuating an image selection switch such as switch 28. On the other hand, the selection can be adapted to different higher-order points of view.

Although the display of the data via display fields is preferred, the display of the actual or stored parameter values by means of a printer can also be appropriate.

It is understood that the foregoing description is that of the preferred embodiments of the invention and that various changes and modifications may be made thereto without departing from the spirit and scope of the invention as defined in the appended claims.

What is claimed is:

1. A method in a computer for monitoring data of a patient and processing said patient data is display processors for selectively displaying said patient data, the method comprising the steps of:

storing a multiplicity of switching combinations in a storage field;

sensing data corresponding to vital signals of the patient with a plurality of sensors;

storing the data in trend memories connected to respective ones of the sensors of collecting a plurality of sets of data with each one of the sets of data relating to one of the vital signs;

selecting a specific one of the switching combinations with an image selection switch connected to the storage field and placing the selected switching combination in an active memory;

configuring a switching matrix, connected to said active memory and to said trend memories, in response to said selected switching combination to select particular ones of said sets of data for a particular organ or organ system;

processing the particular ones of said sets of data for said particular organ or organ system in said display processors, which are connected to said switching matrix, for display with respect to said particular organ or organ system and providing an output indicative of a desired display format for said particular organ or organ system; and selectively connecting the display processors to at least one of a plurality of display fields with a coordinating switch for displaying said display format.

2. The method of claim 1, further comprising the step of selecting said display format to represent said particular ones of said sets of data in the form of a curve plotted as a function of time.

3. The method of claim 1, further comprising the step of selecting said display format to represent trends of the particular ones of said sets of data as functions of time.

4. The method of claim 1, wherein said organ or organ system includes the following: consciousness/central nervous system (CNS), respiratory system, cardiovascular system and metabolic system.

5. The method for claim 1, wherein the display of the display format provides an indication of the status of the patient.

6. The method of claim 1, wherein the display of the display format for said particular organ or organ system provides an actual condition at a point in time.

7. The method of claim 6, wherein the display of the display format further provides an overview of the particular ones of said sets of data for said particular organ or organ system over a previously determined time duration.

8. A circuit arrangement for monitoring data of the patient which are assigned as parameter values to respective individual organs and organ systems, the circuit arrangement comprising:

a plurality of sensors for sensing corresponding ones of a plurality of vital signs of the patient indicative of body functions;

a plurality of trend memories connected to corresponding ones of said sensors for collecting a plurality of sets of data with each one of said sets of data relating to one of said vital signs;

matrix switching means connected to said trend memories for selecting particular ones of said sets of data for a particular organ or organ system for processing;

display processor means connected to said matrix switching means for processing the particular ones of said sets of data for said particular organ or organ system for display with respect to said particular organ or organ system and to provide an output indicative of a desired display format for said particular organ or organ system;

display field means for displaying said display format;

coordinating switch means for connecting said display processor means to said display field means;

storage field for storing a multiplicity of switching combination for selecting said particular ones of said sets of data;

image selection switch means connected to said storage field for selection a specific one of said combinations;

an active memory for receiving the specific one of said combinations; and, said active memory being connected to said matrix switching means for configuring said matrix switching means with respect of the selection of said sets of data and to said coordinating switching means for selectively connecting said display processor means to said display field means.

9. The circuit arrangement of claim 8, said display processor means including first and second sets of display processors connected to said matrix switching means; said display field means including first and second sets of display fields; and, said coordinating switch means including a first set of coordinating switches for interconnecting said first set of display processors and said first set of said display fields, and a second set of coordinating switches interconnecting said second set of display processors and said second set of display fields.

10. The circuit arrangement of claim 8, further comprising:

a computer connected to said storage field for changing said multiplicity of switching combinations;

a key pad connected to said computer for issuing commands to said computer for selecting a particular switching combination from said multiplicity of switching combinations stored in said storage field.

* * * * *

UNITED STATES PATENT AND TRADEMARK OFFICE
CERTIFICATE OF CORRECTION

PATENT NO. : 5,140,519

DATED : August 18, 1992

INVENTOR(S) : Wolfgang Friesdorf, Martin Ryschka and Jörg Bayerlein

It is certified that error appears in the above-identified patent and that said Letters Patent is hereby corrected as shown below:

In column 1, line 23: delete "said" and substitute -- aid -- therefor.

In column 1, line 58: delete "said" and substitute -- aid -- therefor.

In column 3, line 38: delete "said" and substitute -- aid -- therewith.

In column 4, line 45: delete "is" and substitute -- in -- therefor.

In column 4, line 53: delete "of" (second occurrence) and substitute -- for -- therefor.

In column 6, line 11: before "storage", insert -- a --.

In column 6, line 12: delete "combination" and substitute -- combinations -- therefor.

In column 6, line 15: delete "selection" and substitute -- selecting -- therefor.

Signed and Sealed this

Twenty-eighth Day of September, 1993

Attest:

BRUCE LEHMAN

*Attesting Officer*　　*Commissioner of Patents and Trademarks*